United States Patent
Suzuki et al.

(10) Patent No.: US 11,912,783 B2
(45) Date of Patent: Feb. 27, 2024

(54) MONOCLONAL ANTIBODY AGAINST IGM AND NON-SPECIFIC REACTION INHIBITOR

(71) Applicant: TANAKA KIKINZOKU KOGYO K.K., Tokyo (JP)

(72) Inventors: Keita Suzuki, Kanagawa (JP); Hisahiko Iwamoto, Kanagawa (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 732 days.

(21) Appl. No.: 16/971,452

(22) PCT Filed: Feb. 21, 2019

(86) PCT No.: PCT/JP2019/006663
§ 371 (c)(1),
(2) Date: Aug. 20, 2020

(87) PCT Pub. No.: WO2019/163922
PCT Pub. Date: Aug. 29, 2019

(65) Prior Publication Data
US 2020/0399399 A1    Dec. 24, 2020

(30) Foreign Application Priority Data
Feb. 21, 2018    (JP) .................... 2018-029071

(51) Int. Cl.
*C07K 16/42*    (2006.01)
*G01N 33/53*    (2006.01)
*G01N 33/543*    (2006.01)

(52) U.S. Cl.
CPC ..... *C07K 16/4241* (2013.01); *G01N 33/5306* (2013.01); *G01N 33/54386* (2013.01)

(58) Field of Classification Search
None
See application file for complete search history.

(56) References Cited

U.S. PATENT DOCUMENTS

| | | |
|---|---|---|
| 2011/0165701 A1 | 7/2011 | Takahashi et al. |
| 2016/0341721 A1 | 11/2016 | Takahashi et al. |
| 2018/0284115 A1 | 10/2018 | Suzuki et al. |
| 2020/0057055 A1 | 2/2020 | Suzuki et al. |

FOREIGN PATENT DOCUMENTS

| | | |
|---|---|---|
| JP | H11-287801 A | 10/1999 |
| JP | 2016-065795 A | 4/2016 |
| JP | 2017-015533 A | 1/2017 |
| WO | WO-2010/026758 A1 | 3/2010 |
| WO | WO-2018/203572 A1 | 11/2018 |

OTHER PUBLICATIONS

International Searching Authority, "International Search Report," issued in connection with International Patent Application No. PCT/JP2019/006663, dated Mar. 26, 2019, (5 pages).

International Searching Authority, "Written Opinion," issued in connection with International Patent Application No. PCT/JP2019/006663, dated Mar. 26, 2019, (5 pages).

Tipold, A. et al., "Presumed immune-mediated cerebellar granuloprival degeneration in the Coton de Tulear breed", Journal of Neuroimmunology, 2000, pp. 130-133, vol. 110, Elsevier Science B.V.

*Primary Examiner* — Ellen J Marcsisin
(74) *Attorney, Agent, or Firm* — Foley & Lardner LLP

(57) ABSTRACT

An object of the present invention is to provide a monoclonal antibody capable of sufficiently inhibiting a non-specific reaction caused by a non-specific factor, a non-specific reaction inhibitor containing the monoclonal antibody, and the like. The present invention relates to a monoclonal antibody against dog IgM produced by a hybridoma with accession No. NITE BP-02556.

10 Claims, 1 Drawing Sheet

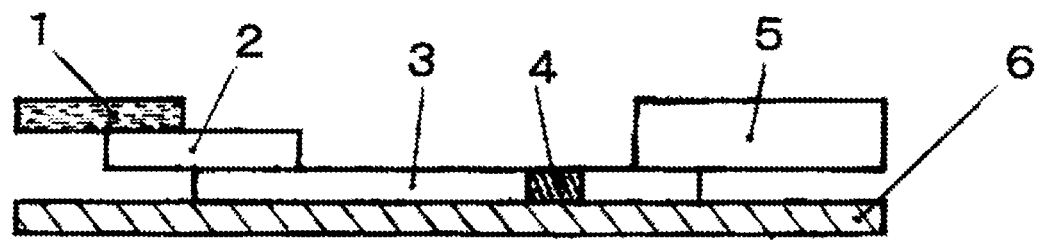

MONOCLONAL ANTIBODY AGAINST IGM AND NON-SPECIFIC REACTION INHIBITOR

CROSS-REFERENCE TO RELATED APPLICATIONS

The present application claims priority under 37 U.S.C. § 371 to International Patent Application No. PCT/JP2019/006663, filed Feb. 21, 2019, which claims priority to and the benefit of Japanese Patent Application No. 2018-029071, filed on Feb. 21, 2018. The contents of these applications are hereby incorporated by reference in their entireties.

TECHNICAL FIELD

The present invention relates to a monoclonal antibody, a non-specific reaction inhibitor for an immunoassay method containing the monoclonal antibody, a test strip for immunochromatography and a test kit for immunochromatography, and an immunoassay method including performing an immunoreaction in the presence of the non-specific reaction inhibitor.

BACKGROUND ART

An immunoassay method using an antigen-antibody reaction is widely used in clinical tests because a minor component can be measured specifically and with high sensitivity. As such an immunoassay method, for example, an enzyme immunoassay method (for example, an ELISA method), an agglutination method, an immunochromatographic method, a radioimmunoassay method, a turbidimetric method, and the like are known.

The antigen-antibody reaction is a binding reaction with high specificity that occurs because an antigen-binding site of an antibody induced to a certain antigenic determinant has high complementarity with the antigenic determinant. However, in an immunoassay using the antigen-antibody reaction, it is often recognized that a non-specific reaction other than the original target specific antigen-antibody reaction occurs and the reliability of measurement values is impaired.

As one of the causes of such a phenomenon, the presence of a component that binds to an antibody used for an immunoassay (hereinafter referred to as a non-specific factor) in a specimen although it is a component other than the detection target (antigen) is exemplified. If such a non-specific factor is present in a specimen, a measurement result showing that a detection target is present although the detection target is not present is obtained.

Such a non-specific factor is a substance which binds not only to an antibody that specifically reacts with a detection target, but also to an antibody that does not react with the detection target. As the non-specific factor, a heterophilic antibody and a rheumatoid factor are known.

The heterophilic antibody is an antibody against an antibody derived from an animal species other than a human present in human blood or the like, and includes not only a human antibody against a mouse antibody (HAMA), but also a human antibody against a goat antibody (HAGA), a human antibody against a sheep antibody (HASA), a human antibody against a rabbit antibody (HARA), and the like.

The rheumatoid factor is an antibody against a human antibody present in human blood or the like, and is an autoantibody often found in patients with rheumatoid arthritis.

Further, it is said that there exist many non-specific factors whose components have not yet become clear other than the heterophilic antibody or the rheumatoid factor.

The presence of the non-specific factor in a specimen impairs the advantage of an immunoassay method that a minor component can be measured specifically and with high sensitivity, and is a serious problem leading to misdiagnosis of a disease in a patient or the like in the clinical laboratory field. Therefore, various attempts have been made in the past to inhibit a non-specific reaction caused by a non-specific factor and obtain a correct measurement value.

In Patent Literature 1, an immunological measurement method capable of inhibiting a non-specific reaction caused by a non-specific factor and accurately measuring an antigen by adding an anti-human IgM antibody or an anti-human IgG antibody that reacts with an IgM-type or IgG-type natural antibody which is a non-specific factor present in a sample to an immunoassay system.

CITATION LIST

Patent Literature

Patent Literature 1: JP-A-H11-287801

SUMMARY OF INVENTION

Technical Problem

However, although the conventional method shows a certain degree of effect of inhibiting a non-specific reaction in an immunoassay method, the effect is not necessarily sufficient, and there is still room for improvement. In addition, depending on the specimen, the effect of a conventionally used non-specific reaction inhibitor is hardly obtained, and there are not a few inhibitors that cannot inhibit a non-specific reaction caused by a non-specific factor, and the method is not always satisfactory in practice.

Therefore, an object of the present invention is to provide a monoclonal antibody capable of sufficiently inhibiting a non-specific reaction caused by a non-specific factor, a non-specific reaction inhibitor for an immunoassay method containing the monoclonal antibody, and the like.

Solution to Problem

As a result of intensive studies, the present inventors conducted an immunoassay method using a monoclonal antibody produced by a specific hybridoma among the monoclonal antibodies that react with dog IgM, resulting in finding out that a non-specific reaction can be sufficiently inhibited, and thus completed the present invention.

Therefore, the present invention is as follows.

1. A monoclonal antibody against dog IgM produced by a hybridoma with accession No. NITE BP-02556.
2. A hybridoma with accession No. NITE BP-02556.
3. A non-specific reaction inhibitor for an immunoassay method, containing the monoclonal antibody according to the above 1.
4. The non-specific reaction inhibitor according to the above 3, wherein a content of the monoclonal antibody is 0.5 µg or more and 20 µg or less.
5. The non-specific reaction inhibitor according to the above 3 or 4, wherein the immunoassay method is an immunochromatographic method.
6. A test strip for immunochromatography, containing the non-specific reaction inhibitor according to any one of the above 3 to 5.
7. A test kit for immunochromatography, containing the non-specific reaction inhibitor according to any one of the above 3 to 5.
8. An immunoassay method, including performing an immunoreaction in the presence of the non-specific reaction inhibitor according to any one of the above 3 to 5 in an immunoassay method for specifically detecting a detection target in a specimen.

9. The immunoassay method according to the above 8, wherein the immunoassay method is an enzyme immunoassay method, an agglutination method, or an immunochromatographic method.

10. The immunoassay method according to the above 8, wherein the immunoassay method is an immunochromatographic method.

Advantageous Effects of Invention

By using the monoclonal antibody and the non-specific reaction inhibitor containing the monoclonal antibody of the present invention, a non-specific reaction in an immunoassay method can be inhibited.

BRIEF DESCRIPTION OF DRAWINGS

The FIGURE is a view showing an embodiment of a test strip for immunochromatography containing a non-specific reaction inhibitor of the present invention.

DESCRIPTION OF EMBODIMENTS

Hereinafter, the present invention will be described in detail, however, the present invention is by no means limited to the following embodiments and can be implemented with appropriate modifications within the scope of the object of the present invention.

The monoclonal antibody that is an embodiment of the present invention is a monoclonal antibody against dog IgM produced by a hybridoma (Anti-Dog IgM No. 12) with accession No. NITE BP-02556. The dog IgM means an IgM-type immunoglobulin derived from a dog.

The present applicant deposited the hybridoma (Anti-Dog IgM No. 12) obtained by a method described in the below-mentioned Examples at the National Institute of Technology and Evaluation, Patent Microorganisms Depositary. The contents specifying the deposit are described below.

The present applicant deposited the hybridoma (Anti-Dog IgM No. 12) under the following conditions.
(1) Depositary institution name: National Institute of Technology and Evaluation, Patent Microorganism Depositary
(2) Contact: #122, 2-5-8 Kazusa Kamatari Kisarazu-shi, Chiba-ken 292-0818, Japan, Phone number: 0438-20-5580
(3) Accession No.: NITE BP-02556
(4) Indication for identification: Anti-Dog IgM No. 12
(5) Date of original deposit: Oct. 10, 2017

By using the monoclonal antibody in a state of being incorporated in a non-specific reaction inhibitor, a non-specific reaction in an immunoassay method can be sufficiently inhibited.

The non-specific reaction inhibitor containing the monoclonal antibody may be composed only of the monoclonal antibody, or may contain another component other than the monoclonal antibody within a range not impairing the effect of the present invention. Examples of the another component include phosphates, buffers such as trishydroxymethylaminomethane, preservatives such as sodium azide, inorganic salts such as sodium chloride and potassium chloride, and the like.

The form of the non-specific reaction inhibitor that is an embodiment of the present invention is not particularly limited, and may be a solid or a liquid. In the case of a liquid, it can be prepared by dissolving or suspending a component contained in the non-specific reaction inhibitor in a solvent. Examples of the solvent include water, organic solvents such as glycerol, mixed solvents thereof, and the like.

The content of the monoclonal antibody in the non-specific reaction inhibitor that is an embodiment of the present invention is not particularly limited, and can be appropriately adjusted based on the type of the specimen, the amount of the specimen, the measurement conditions of the immunoassay method, or the like. For example, the content of the monoclonal antibody in the non-specific reaction inhibitor to be used per specimen is preferably 0.5 µg or more and 20 µg or less, more preferably 1 µg or more and 15 µg or less, and further more preferably 2 µg or more and 10 µg or less from the viewpoint of the inhibitory effect on the non-specific reaction.

The immunoassay method to which the non-specific reaction inhibitor that is an embodiment of the present invention can be applied is not particularly limited and can exhibit its effect as long as it is a method for measuring a detection target in a specimen using an immunoreaction. For example, an enzyme immunoassay method (for example, an ELISA method), an agglutination method, an immunochromatographic method, a radioimmunoassay method, a turbidimetric method, and the like are exemplified, and an enzyme immunoassay method, an agglutination method, or an immunochromatographic method is preferred. The non-specific reaction inhibitor that is an embodiment of the present invention is particularly useful for an immunochromatographic method that is considered to be easy to handle due to the ease of collecting a specimen.

Next, the test strip for immunochromatography that is an embodiment of the present invention will be described. The test strip for immunochromatography that is an embodiment of the present invention contains the non-specific reaction inhibitor.

The test strip for immunochromatography that is an embodiment of the present invention can be used, for example, for determining the presence or absence of a detection target or for measuring the concentration of a detection target using an immunochromatographic method.

The test strip for immunochromatography that is an embodiment of the present invention is not particularly limited except that it contains the non-specific reaction inhibitor, and can be configured in the same manner as a known test strip for immunochromatography. In the present invention, the non-specific reaction inhibitor may be contained in such a state that it can be involved in the immunoreaction in a member in which a liquid phase containing a specimen is developed by a capillary phenomenon among the members constituting the test strip for immunochromatography. According to this, the immunoreaction can be performed in the presence of the non-specific reaction inhibitor, and the non-specific reaction can be sufficiently inhibited.

Hereinafter, an embodiment of the test strip for immunochromatography of the present invention will be described with reference to the drawing, however, the test strip for immunochromatography of the present invention is not limited to the following embodiment.

An embodiment of the test strip for immunochromatography of the present invention shown in the FIGURE includes a sample pad 1, a conjugate pad 2, a membrane pad 3, an absorption pad 5, and a backing sheet 6.

The sample pad 1 is a member provided for adding a sample containing a specimen and allowing the sample to migrate downstream by a capillary phenomenon. As a material of the sample pad 1, a known material can be used, and examples thereof include ceramic fine particles of silica, titania, zirconia, ceria, alumina, and the like, polyurethane, polyester, polyethylene, polyvinyl chloride, polyvinylidene fluoride, nylon, nitrocellulose, cellulose acetate, glass fiber, cotton, and the like. Further, the size and shape of the sample pad 1 are not particularly limited, and may be any size and shape as long as they are appropriate in terms of the actual operation and the observation of the reaction result. It is also possible to make the sample pad 1 have the function of the below-mentioned conjugate pad.

The conjugate pad 2 is a member containing a labeling reagent in which an antibody or an antigen that specifically reacts with a detection target in a specimen is labeled with a labeling substance. When a sample containing the specimen passes through the conjugate pad 2, a complex of the detection target and the labeling reagent is formed. As a material of the conjugate pad 2, a known material can be used, and examples thereof include ceramic fine particles of silica, titania, zirconia, ceria, alumina, and the like, polyurethane, polyester, polyethylene, polyvinyl chloride, polyvinylidene fluoride, nylon, nitrocellulose, cellulose acetate, glass fiber, cotton, and the like. Further, the size and shape of the conjugate pad 2 are not particularly limited, and may be any size and shape as long as they are appropriate in terms of the actual operation and the observation of the reaction result.

The labeling substance is not particularly limited, and for example, a known substance such as metal nanoparticles of gold, silver, platinum, or the like, or latex particles can be used. The average particle diameter of the metal nanoparticles is not particularly limited, but is preferably 10 nm or more and 150 nm or less, more preferably 20 nm or more and 100 nm or less. Further, the average particle diameter of the latex particles is not particularly limited, but is preferably 100 nm or more and 500 nm or less, and more preferably 100 nm or more and 250 nm or less. Since the presence or absence of the detection target in the specimen can be visually determined, the labeling substance is preferably gold nanoparticles.

As the antibody or the antigen in the labeling reagent, a commercially available antibody or antigen can be used as long as it can specifically bind to the detection target in the specimen, and one prepared according to need can be used. When the detection target is an antigen, an antibody that can specifically bind to the antigen is preferred. The antibody may be a monoclonal antibody or a polyclonal antibody. Such an antibody can be produced by a known method, for example, through sensitization of an animal to an antigen that is the detection target. Specific examples of the animal species can include, but are not limited to, a mouse, a rat, a guinea pig, a dog, a goat, sheep, a pig, a horse, a cow, a human, and the like.

The content of the antibody or the antigen in the labeling reagent is not particularly limited, but is preferably 0.01 m or more and 10 μg or less, more preferably 0.02 m or more and 5 μg or less, and further more preferably 0.02 μg or more and 1 μg or less per test strip.

The membrane pad 3 is a member having a detection part 4 for determining the presence or absence of a detection target, or the like, or measuring the concentration of the detection target by detecting the detection target. To the detection part 4, a capture reagent containing an antibody or an antigen for capturing the detection target is fixed. In the detection part 4, when the detection target is contained in the specimen, a complex composed of the labeling reagent, the detection target, and the capture reagent is formed and a color is developed, and when the detection target is not contained in the specimen, a complex composed of the labeling reagent, the detection target, and the capture reagent is not formed, and therefore, a color is not developed.

As a material of the membrane pad 3, a known material can be used, and examples thereof include ceramic fine particles of silica, titania, zirconia, ceria, alumina, and the like, polyurethane, polyester, polyethylene, polyvinyl chloride, polyvinylidene fluoride, nylon, nitrocellulose, cellulose acetate, glass fiber, cotton, and the like. Further, the size and shape of the membrane pad 3 are not particularly limited, and may be any size and shape as long as they are appropriate in terms of the actual operation and the observation of the reaction result.

The antibody or the antigen used for the capture reagent may be the same antibody or antigen as the antibody or the antigen contained in the labeling reagent, or may be a different antibody or antigen.

As the antibody or the antigen used for the capture reagent, a commercially available antibody or antigen can be used as long as it can specifically bind to the detection target in the specimen, and one prepared according to need can be used. When the detection target is an antigen, an antibody that can specifically bind to the antigen is preferred. The antibody may be a monoclonal antibody or a polyclonal antibody. Such an antibody can be produced by a known method through sensitization of an animal to an antigen that is the detection target. Specific examples of the animal species can include, but are not limited to, a mouse, a rat, a guinea pig, a dog, a goat, sheep, a pig, a horse, a cow, a human, and the like.

The content of the antibody or the antigen used for the capture reagent is not particularly limited, but is preferably 0.1 μg or more and 10 μg or less, more preferably 0.2 μg or more and 5 μg or less, and further more preferably 0.2 μg or more and 4 μg or less per test strip.

The shape of the detection part is not particularly limited, and examples thereof include a linear shape, a circular shape, and the like. From the viewpoint of visibility and detection efficiency, a linear shape is preferred.

The membrane pad 3 can be subjected to a blocking treatment by a known method as needed so as to prevent a decrease in the accuracy of analysis due to non-specific adsorption. In general, a protein such as bovine serum albumin, skim milk, casein, or gelatin is preferably used for the blocking treatment. After such a blocking treatment, washing may be performed using one surfactant or a combination of two or more surfactants such as Tween™ 20, Triton™ X-100, and SDS as needed.

The absorption pad 5 is a member that absorbs an excess amount of the sample or the like that has passed through the membrane pad 3. As a material of the absorption pad, a known material can be used, and examples thereof include ceramic fine particles of silica, titania, zirconia, ceria, alumina, and the like, polyurethane, polyester, polyethylene, polyvinyl chloride, polyvinylidene fluoride, nylon, nitrocellulose, cellulose acetate, glass fiber, cotton, and the like. Further, the size and shape of the absorption pad 5 are not particularly limited, and may be any size and shape as long as they are appropriate in terms of the actual operation and the observation of the reaction result.

The backing sheet 6 is a member used as a support for fixing the respective members such as the sample pad 1, the conjugate pad 2, the membrane pad 3, and the absorption pad 5. A material of the backing sheet is not particularly limited, and for example, conventionally known various materials that become impermeable to a sample and impermeable to moisture by an adhesive can be used. Further, the size and shape of the backing sheet 6 are not particularly limited, and may be any size and shape as long as they are appropriate in terms of the actual operation and the observation of the reaction result.

In an embodiment of the test strip for immunochromatography of the present invention, the non-specific reaction inhibitor is contained in at least one of the sample pad 1, the conjugate pad 2, and the membrane pad 3.

The content of the monoclonal antibody in the non-specific reaction inhibitor contained in the test strip for immunochromatography that is an embodiment of the present invention is not particularly limited. From the viewpoint of the inhibitory effect on the non-specific reaction, it is preferably 0.5 μg or more and 20 μg or less, more preferably 1 μg or more and 15 μg or less, and further more preferably, 2 μg or more and 10 μg or less per test strip. When the content is in the above range, the non-specific reaction can be strongly inhibited.

Next, the test kit for immunochromatography that is an embodiment of the present invention will be described.

In the present invention, the test kit refers to a kit including two or more articles such as a reagent necessary for an immunoassay. The test kit for immunochromatography that is an embodiment of the present invention is not particularly limited except that it contains the non-specific reaction inhibitor, and can be configured in the same manner as a known test kit for immunochromatography.

In the present invention, the non-specific reaction inhibitor may be contained in the test kit for immunochromatography in such a state that it can be involved in the immunoreaction. For example, the non-specific reaction inhibitor may be contained independently as a reagent, or may be contained in advance in a reagent such as a specimen diluent used for the immunoassay, a test strip, or the like.

In an embodiment of the present invention, the test kit for immunochromatography includes a reagent necessary for the immunoassay in addition to the test strip. The test strip is not particularly limited, and for example, a test strip composed of the sample pad, the conjugate pad, the membrane pad, the absorption pad, the backing sheet, or the like can be used. The reagent necessary for the immunoassay is not particularly limited, but examples thereof include a sample diluent, a developing solution, and the like.

In an embodiment of the present invention, the non-specific reaction inhibitor is contained in at least one of the test strip and the reagent. More specifically, the non-specific reaction inhibitor is contained in at least one of the sample pad, the conjugate pad, the membrane pad, and the reagent. By doing this, an antigen-antibody reaction can be performed in presence of the non-specific reaction inhibitor, and the non-specific reaction can be inhibited.

The content of the monoclonal antibody in the non-specific reaction inhibitor contained in the test kit for immunochromatography that is an embodiment of the present invention is not particularly limited. From the viewpoint of the inhibitory effect on the non-specific reaction, it is preferably 0.5 µg or more and 20 µg or less, more preferably 1 µg or more and 15 µg or less, and further more preferably 2 µg or more and 10 µg or less per test kit. When the content is in the above range, the non-specific reaction can be efficiently inhibited without increasing the viscosity of the solution.

Next, the immunoassay method that is an embodiment of the present invention will be described.

The immunoassay method that is an embodiment of the present invention is configured to perform an immunoreaction in the presence of the non-specific reaction inhibitor. The immunoassay method that is an embodiment of the present invention can inhibit a non-specific reaction other than the original target immunoreaction by performing the immunoreaction in the presence of the non-specific reaction inhibitor.

The immunoassay method that is an embodiment of the present invention is not particularly limited as long as it is a method for quantitatively or qualitatively measuring a detection target in a specimen using an immunoreaction. For example, an enzyme immunoassay method (for example, an ELISA method), an agglutination method, an immunochromatographic method, a radioimmunoassay method, a turbidimetric method, and the like are exemplified, and an enzyme immunoassay method, an agglutination method, or an immunochromatographic method is preferred. The immunoassay method that is an embodiment of the present invention is particularly useful for an immunochromatographic method that is considered to be easy to handle due to the ease of collecting a specimen.

The specimen used for the immunoassay method that is an embodiment of the present invention is not particularly limited, and examples thereof include serum, plasma, whole blood, urine, saliva, nasal discharge, and the like.

As the detection target which can be measured in the immunoassay method that is an embodiment of the present invention, for example, a virus, a bacterium, a parasite, a metabolite, and the like contained in a specimen are exemplified, and more specifically, a protein, a peptide, a polysaccharide, a complex carbohydrate, and the like included therein can be exemplified. In particular, an antigen contained in a trace amount in a specimen is preferred. This is because the smaller the concentration of the antigen contained in the specimen is, the relatively greater the effect of the non-specific reaction is, so that the non-specific reaction inhibitor that is an embodiment of the present invention becomes useful.

The immunoreaction in the present invention is not particularly limited as long as it is performed in the presence of the non-specific reaction inhibitor, and can be performed according to a conventional method. For example, the immunoreaction can be performed by bringing the specimen and the non-specific reaction inhibitor into contact with each other in advance before performing the immunoreaction, and then bringing the resultant into contact with an antibody or an antigen that can bind to the detection target in the specimen. Further, the immunoreaction can be performed by bringing an antibody or an antigen that can bind to the detection target in the specimen and the non-specific reaction inhibitor into contact with each other in advance before performing in the immunoreaction, and then bringing the resultant into contact with the specimen.

The content of the monoclonal antibody in the non-specific reaction inhibitor used in the present invention is not particularly limited, and can be appropriately adjusted based on the type of the specimen, the amount of the specimen, the measurement conditions of the immunoassay method, or the like. For example, the content of the monoclonal antibody in the non-specific reaction inhibitor to be used per specimen is preferably 0.5 µg or more and 20 µg or less, more preferably 1 µg or more and 15 µg or less, and further more preferably 2 µg or more and 10 µg or less from the viewpoint of the inhibitory effect on the non-specific reaction.

When the immunoassay method that is an embodiment of the present invention is an immunochromatographic method, for example, a sample obtained by adding the non-specific reaction inhibitor in advance to a specimen containing an antigen is added to a solid phase, and an immune complex is formed in the solid phase, whereby the antigen can be detected. In addition, a specimen containing an antigen is developed in a solid phase such as the sample pad or the conjugate pad to which the non-specific reaction inhibitor is added in advance, and an immune complex is formed in the solid phase, whereby the antigen can be detected.

When the immunoassay method that is an embodiment of the present invention is an enzyme immunoassay method (for example, an ELISA method), for example, the non-specific reaction inhibitor is added in advance to a specimen containing an antigen, and then an antigen-antibody reaction is performed according to a conventional method, whereby the concentration of the antigen can be measured.

When the immunoassay method that is an embodiment of the present invention is an agglutination method, for example, in the case of a latex agglutination turbidimetric method, the non-specific reaction inhibitor may be added in advance into a specimen containing an antigen, or may be added in advance into a latex turbid solution. The latex agglutination turbidimetric method can be performed by a conventional method.

EXAMPLES

Hereinafter, the present invention will be described in detail based on Examples, however, the present invention is by no means limited to the following Examples.

[Preparation of Antibody]

A monoclonal antibody of an anti-dog IgM antibody was prepared according to a conventional method as follows using dog IgM (manufactured by Rockland Immunochemicals, Inc., product name: DOG IgM Whole molecule) as an immunogen. 100 μg of the above dog IgM and an equal amount of Adjuvant Complete Freund (Difco) were mixed, and a mouse (BALB/c, at 5 weeks of age, Japan SLC) was immunized three times, and the spleen cells of the mouse were used for cell fusion. In the cell fusion, Sp2/0-Ag14 cells (Shulman et al., Nature, 276, 269-270, 1978), which are mouse myeloma cells, were used. In cell culture, a culture medium obtained by adding L-glutamine at 0.3 mg/mL, penicillin G potassium at 100 units/mL, streptomycin sulfate at 100 μg/mL, and Gentacin at 40 μg/mL to Dulbecco's Modified Eagle Medium (Gibco) (DMEM), and then adding fetal bovine serum (JRH) thereto at 10% was used. The cell fusion was performed by mixing the spleen cells of the immunized mouse and the Sp2/0-Ag14 cells and adding a polyethylene glycol solution (Sigma) thereto. The fused cells were cultured in HAT-DMEM [serum-supplemented DMEM containing 0.1 mM sodium hypoxanthine, 0.4 μM aminopterine, and 0.016 mM thymidine (Gibco)], and the production of the antibody in the culture supernatant was confirmed by an enzyme immunoassay method (ELISA method). Cells that are positive for antibody production were cultured in HT-DMEM [serum-supplemented DMEM containing 0.1 mM sodium hypoxanthine and 0.16 mM thymidine], and further kept cultured in serum-supplemented DMEM.

The cloned cells were intraperitoneally inoculated into a mouse (BALB/c, Retire, Japan SLC) which had been inoculated with 2,6,10,14-tetramethylpentadecane (Sigma), and the ascites was collected. This ascites was applied to a protein G column to purify the monoclonal antibody. Among the obtained antibodies, 4 types of monoclonal antibodies (Nos. 12, 32, 70, and 80) were used in the below-mentioned test. The isotype thereof was IgG type. Among these, No. 12 is a monoclonal antibody against dog IgM produced by the hybridoma with accession No. NITE BP-02556 described above.

[Non-Specific Reaction Inhibition Test]

By using human serum exhibiting a non-specific reaction as a specimen, the non-specific reaction inhibitory effect of the immunoassay method using the monoclonal antibody prepared above and a conventionally known heterophilic blocking reagent HBR was evaluated.

Specifically, as shown in the FIGURE, a test strip in which a membrane pad 3 having a detection part 4, a sample pad 1, a conjugate pad 2, and an absorption pad 5 were formed on a backing sheet 6, and a sample to be developed were prepared as follows, and measurement was performed by an immunochromatographic method to evaluate the non-specific reaction inhibitory effect.

(1) Preparation of Sample Pad

As the sample pad, a nonwoven fabric composed of glass fiber (manufactured by Millipore, Inc. 300 mm×30 mm) was used.

(2) Preparation of Conjugate Pad

To 0.5 mL of a colloidal gold suspension (manufactured by Tanaka Kikinzoku Kogyo K.K., LC 40 nm), 0.1 mL of an anti-Zika virus NS1 antibody (manufactured by Aalto Bio Reagents Ltd., product name: Anti-Zika Virus NS1 Antibody) diluted to a concentration of 0.05 mg/mL with a phosphate buffer solution (pH 7.4) was added, and the resulting mixture was left to stand at room temperature for 10 minutes.

Subsequently, 0.1 mL of a phosphate buffer solution (pH 7.4) containing 1 mass % bovine serum albumin (BSA) was added thereto, and the resulting mixture was left to stand at room temperature for an additional 10 minutes. Thereafter, the mixture was thoroughly stirred, and then centrifuged at 8000×g for 15 minutes. After removing the supernatant, 0.1 mL of a phosphate buffer solution (pH 7.4) containing 1 mass % BSA was added thereto. According to the above-mentioned procedure, a labeling reagent was prepared.

A solution obtained by adding 300 μL of a 10 mass % trehalose aqueous solution and 1.8 mL of distilled water to 300 μL of the labeling reagent prepared above was added uniformly to a 12 mm×300 mm glass fiber pad (manufactured by Millipore, Inc.), followed by drying in a vacuum dryer, whereby a conjugate pad was prepared.

(3) Preparation of Detection Part

As a membrane, a sheet composed of nitrocellulose (manufactured by Millipore, Inc., trade name: HF120, 300 mm×25 mm) was used.

Subsequently, 150 μL of a solution obtained by diluting an anti-Zika virus NS1 antibody (manufactured by Aalto Bio Reagents Ltd., product name: Anti-Zika Virus NS1 Antibody) to a concentration of 1.0 mg/mL with a phosphate buffer solution (pH 7.4) containing 5 mass % isopropyl alcohol was applied in a line shape with a width of 1 mm in an amount of 1 μL/mm (25 μL per sheet) to the detection part on the dried membrane using a dispenser for immunochromatography "XYZ3050" (manufactured by BioDot, Inc.).

Further, in order to confirm the presence or absence of development of the gold nanoparticle labeling reagent or the developing rate, on the downstream of the detection part, a solution obtained by diluting a goat-derived antiserum having affinity in a wide range for the gold nanoparticle labeling substance with a phosphate buffer solution (pH 7.4) was applied to a control region (control line). Thereafter, the solution was dried at 50° C. for 30 minutes, and then dried overnight at room temperature.

(4) Preparation of Test Strip

The sample pad, the conjugate pad, and an absorption pad composed of a nonwoven fabric made of glass fiber were sequentially bonded to the membrane pad having the detection part. Then, the resulting material was cut to a width of 5 mm by a cutting machine and bonded onto a backing sheet (manufactured by Kuramoto Sangyo Co., product name: backing sheet for immunochromatography), whereby a test strip was prepared. Note that the length in the sample developing direction of the conjugate pad was set to 12 mm.

(5) Preparation of Sample to be Developed

Human serum exhibiting a non-specific reaction (manufactured by SCIPAC Ltd., product name: Normal Female Serum) was used as a specimen, and 30 μL of the specimen, 60 μL of a PBS solution containing 0.5% Triton™ X-100, and 4 μg of the monoclonal antibody of Example or Comparative Example prepared above, or 4 μg of HBR (manufactured by Scantibody, Inc.) were mixed, whereby a sample to be developed was prepared. In addition, a material obtained by using 10 μL of PBS in place of the antibody was used as a control.

(6) Measurement

The non-specific reaction inhibitory effect was tested in the following manner using the test strip and the sample to be developed prepared above.

150 μL of the sample to be developed was added to the sample pad of the test strip and developed, and after 15 minutes, the developed color intensity (the absorbance at 450 nm) of the detection part was measured using an immunochromatographic reader. The results are shown in Table 1.

Further, a determination method is shown below.

A: The color development in the detection part is not visually recognized.

B: The color development in the detection part is visually recognized.

TABLE 1

| | Example 1 | Comparative Example 1 | Comparative Example 2 | Comparative Example 3 | HBR | Control |
|---|---|---|---|---|---|---|
| Antibody | No. 12 (NITE BP-02556) | No. 70 | No. 80 | No. 32 | — | — |
| Developed color intensity (mAbs) | 10.1 | 39.7 | 46.8 | 65.2 | 58.4 | 85.4 |
| Determination | A | B | B | B | B | B |

As can be seen also from the result of the control, it is found that human serum (manufactured by SCIPAC Ltd., product name: Normal Female Serum) used as the specimen is a specimen in which a non-specific reaction occurs. Then, in Example using the antibody according to the present invention, the non-specific reaction could be remarkably inhibited even as compared with the antibodies of Comparative Examples or the heterophilic blocking reagent HBR.

While the present invention has been described in detail with reference to specific embodiments, it is apparent to those skilled in the art that various changes and modifications can be made without departing from the spirit and scope of the present invention. The present application is based on Japanese Patent Application (Japanese Patent Application No. 2018-029071) filed on Feb. 21, 2018, the entire contents of which are incorporated herein by reference.

REFERENCE SIGNS LIST 1. sample pad
2. conjugate pad
3. membrane pad
4. detection part
5. absorption pad
6. backing sheet

The invention claimed is:

1. A monoclonal antibody against dog IgM produced by a hybridoma with accession No. NITE BP-02556.

2. A hybridoma with accession No. NITE BP-02556.

3. A non-specific reaction inhibitor for an immunoassay method, comprising the monoclonal antibody according to claim 1.

4. The non-specific reaction inhibitor according to claim 3, wherein a content of the monoclonal antibody in the non-specific reaction inhibitor is from 0.5 μg to 20 μg or less.

5. The non-specific reaction inhibitor according to claim 3, wherein the immunoassay method is an immunochromatographic method.

6. A test strip for immunochromatography, comprising the non-specific reaction inhibitor according to claim 3.

7. A test kit for immunochromatography, comprising the non-specific reaction inhibitor according to claim 3.

8. An immunoassay method, comprising performing an immunoreaction in the presence of the non-specific reaction inhibitor according to claim 3 in an immunoassay method for specifically detecting a detection target in a specimen.

9. The immunoassay method according to claim 8, wherein the immunoassay method is an enzyme immunoassay method, an agglutination method, or an immunochromatographic method.

10. The immunoassay method according to claim 8, wherein the immunoassay method is an immunochromatographic method.

* * * * *